(12) United States Patent
Gonon

(10) Patent No.: US 6,322,533 B1
(45) Date of Patent: Nov. 27, 2001

(54) APPARATUS FOR TWO-PATH DISTRIBUTION OF A STERILE OPERATING FLUID ACCORDING TO PREDETERMINED SEQUENCES BY MEANS OF AT LEAST ONE HANDPIECE FOR SURGICAL OR MEDICAL USE

(75) Inventor: Bertrand Gonon, Lyons (FR)

(73) Assignee: Saphir Medical, Dardilly (FR)

(*) Notice: Subject to any disclaimer, the term of this patent is extended or adjusted under 35 U.S.C. 154(b) by 0 days.

(21) Appl. No.: 09/338,804

(22) Filed: Jun. 23, 1999

(30) Foreign Application Priority Data

Jun. 24, 1998 (FR) .................................................. 98 08183

(51) Int. Cl.⁷ ....................................................... A61M 1/00
(52) U.S. Cl. ............................................................ 604/35
(58) Field of Search .................................. 604/35, 22, 30, 604/31, 32, 33, 34, 36, 43, 119, 150, 152

(56) References Cited

U.S. PATENT DOCUMENTS

| | | | |
|---|---|---|---|
| 4,205,677 | 6/1980 | Engstrom | 128/276 |
| 4,519,385 | 5/1985 | Atkinson et al. | 128/66 |
| 4,655,197 | 4/1987 | Atkinson et al. | 128/66 |
| 4,676,779 | 6/1987 | Mayoral . | |
| 4,702,733 | 10/1987 | Wright et al. . | |
| 4,759,349 | 7/1988 | Betz et al. | 128/6 |
| 5,322,506 | 6/1994 | Kullas . | |
| 5,605,537 | 2/1997 | Ivey . | |
| 5,674,226 | 10/1997 | Doherty et al. | 606/107 |
| 5,735,815 | 4/1998 | Bair | 604/51 |

FOREIGN PATENT DOCUMENTS

| | | |
|---|---|---|
| 30 19 115 A1 | 12/1981 | (DE) . |
| 37 15 418 A | 11/1987 | (DE) . |
| 0 346 712 A2 | 12/1989 | (EP) . |
| 0 470 781 A1 | 2/1992 | (EP) . |
| 0 489 496 A | 6/1992 | (EP) . |
| 0 489 496 A1 | 6/1992 | (EP) . |
| 0 551 920 A1 | 7/1993 | (EP) . |
| 0 636 345 A1 | 2/1995 | (EP) . |
| 0 879 578 A1 | 11/1998 | (EP) . |
| 0 888 750 A1 | 1/1999 | (EP) . |
| 1 378 042 | 2/1965 | (FR) . |
| 2 706 276 | 12/1994 | (FR) . |
| WO 94/10917 | 5/1994 | (WO) . |
| WO 94 28807 | 12/1994 | (WO) . |
| WO 96/01079 | 1/1996 | (WO) . |
| WO 96/35469 | 11/1996 | (WO) . |
| WO 96/39952 | 12/1996 | (WO) . |
| 97/03713 | 2/1997 | (WO) . |
| WO 97/49441 | 12/1997 | (WO) . |
| WO 98/55033 | 12/1998 | (WO) . |
| WO 99/33510 | 7/1999 | (WO) . |

*Primary Examiner*—Manuel Mendez
(74) *Attorney, Agent, or Firm*—Armstrong, Westerman, Hattori, McLeland & Naughton, LLP

(57) ABSTRACT

The apparatus connects to a pressurized sterile liquid source SOSPE and to an aspiration source SOSPI and is composed of two basic channels, one for a pressurized sterile liquid jet Jet HP for dissection and the other for a flow jet Jet DEBIT for lavage/rinsing or irrigation, with each channel linked to a specific handpiece. Each of the dissection and the lavage/rinsing channels passes through a flow control unit ESCA1 and ESCA2, respectively, which provides for the opening/closing of the fluid links in continuous or pulsed operation making it possible to operate as a pulsed jet or to obtain a continuous jet. This invention applies primarily to manufacturers of apparatuses for medical or surgical use.

24 Claims, 5 Drawing Sheets

APPARATUS FOR TWO-PATH DISTRIBUTION OF A STERILE OPERATING FLUID ACCORDING TO PREDETERMINED SEQUENCES BY MEANS OF AT LEAST ONE HANDPIECE FOR SURGICAL OR MEDICAL USE

The present invention concerns an apparatus for distribution under controlled pressure and flow of a sterile liquid within a broad range of pressures and according to predefined sequences in pulsed or continuous operation for at least one hand unit intended for medical and surgical applications.

BACKGROUND OF THE INVENTION

The technique of aqua dissection, which uses a high-pressure sterile liquid jet fed to a simple hand unit or to one with aspiration like that described in the published patent application WO 9703713 by SAPHIR MEDICAL, is known.

The action of the high-pressure liquid is a tissue cutting action which is more or less incisive depending on the pressure value.

There are other hand units which are used for rinsing or for lavage, with the sterile liquid distributed in that case under low pressure with adjustable flow.

The sterile liquid is delivered by a source adjustable either in pressure or in flow, for example, that of the generator described in publication WO 9428807 by SAPHIR MEDICAL.

This generator comprises a leak-proof chamber enclosing a flexible pouch containing the sterile liquid. The inner volume of the chamber is adjustably pressurized with a neutral gas. The pneumatic force of this gas expels the sterile liquid from the pouch to the output line. Depending on the hand unit type, i.e., dissection or lavage/rinsing, the liquid coming out is used under pressure or in flow, respectively.

This generator enables successive performance of the two functions corresponding to these two categories of applications. Switching from one to the other necessitates a modification of the tubing and of the hydraulic component.

Thus, this continuous flow generator is limited to distributing sterile liquid by a single type of action at one time, either dissection or lavage/rinsing.

Moreover, the jet is continuous and the generator was provided to feed only a single handpiece at a time.

Thus, it is necessary to change the mode of operation and the conduits each time a switch is made from pressure operation to flow operation, i.e., from the use of a dissection handpiece to a lavage/rinsing unit and vice versa.

The work is performed under aspiration of the operating liquid through the aspiration network, for example, that of the operating theater connected to the evacuation via a vacuum pump.

As the generator is a continuous source, the applications remain limited to those of a continuous jet with adjustable pressure or to diffusion by spraying for the purposes of lavage/rinsing or of irrigation.

Moreover, the advantages of pulsed jets which enable improvement of the precision of dissection work while reducing the pressure and the consumption of the liquid are known in surgery.

This work results from successive sets or trains of periodic pressurized liquid firing pulses, with the pause between the successive sets used for aspiration of the liquid fired and of the biological residues.

Although this pulsed operation enables improvement of the precision of the dissection, the depth of the incision is difficult to control, and efficacy is difficult to guarantee in shallow dissections. Moreover, the visibility of the operative field could be appreciably improved.

SUMMARY OF THE INVENTION

The present invention concerns an apparatus which operates with any type of pressurized liquid sources or generators and with any type of aspiration means. Provision is also made for operation with any type of handpieces controlled manually in various ways, in particular by pneumatic discontinuity.

The apparatus according to invention also targets all medical and surgical applications in which a jet or addition of sterile liquid is used to perform cutting, shaping, cleaning, rinsing, irrigation, or any other work.

Aquadissection, tissue lavage, irrigation of a natural cavity of the human body, shaping of masses of flesh in cosmetic surgery, tumor disintegration, and numerous other examples can be cited.

The distribution apparatus according to the invention is intended to be universal for medical and surgical applications because it can supply handpieces with different functional characteristics depending on the type of work required. It can be used within the framework of cardiac or liver surgery or any other surgical operation and for pulverization and evacuation of a tumor, each of which requires special, different handpieces and specific operating conditions and jet forms.

For example, the work of dissection and disintegration of a tumor is performed under constant suction designed to evacuate not only the liquid used for the cutting or disintegration but also the residues such as tissues, cells, and organic matter and liquids.

To accomplish this, the handpieces include two paths or channels, one for dissection, connected to the pressurized sterile liquid, and the other for evacuation, connected to the depression source.

In its basic version, the sterile liquid distribution apparatus is connected to a pressurized liquid source and to aspiration means and is made up of the following general means:

a pressurized liquid distribution channel connected to a dissection handpiece for operation in pulsed-aspirated or continuous mode;

a flowing liquid distribution channel connected to a lavage/rinsing or irrigation handpiece for operation under continuous manual control;

a control module generating a periodic pulsed pattern of opening/closing of flows in the pressure channel according to predefined sequences;

specific functions enabling the handpiece to be manually controlled by pneumatic discontinuity.

More specifically and more completely, the major functions of the apparatus may be summarized descriptively as follows.

First, the distributor includes at least two different channels, each of which is connected to a dissection handpiece, on the one hand, and to a lavage/rinsing handpiece, on the other hand.

A. The dissection channel includes:

a pressurized sterile liquid distribution conduit connected to a dissection handpiece;

a depression conduit connected to the dissection handpiece;

sequential synchronized means for periodic opening/ closing of the depression, acting on the depression conduit;

means for periodic aeration of the depression synchronized with the first, acting on the depression channel;

synchronized means for periodic opening/closing of the pressurized dissection liquid.

The periodic opening/closing control means can be mutually synchronized for common pulsed operation according to a modifiable cyclic program.

The control means can be deactivated to switch to continuous operation.

B. The lavage/rinsing channel includes:

a sterile liquid distribution conduit with adjustable flow connected to a lavage/rinsing or irrigation handpiece;

a conduit with adjustable depression connected to the same lavage/rinsing handpiece;

means for adjusting the flow of the sterile liquid and the depression;

manual control means for opening/closing the liquid flow;

manual control means for opening/closing the depression connected to the preceding liquid control means.

This entirely novel apparatus has numerous advantages of which a few will be indicated in the following:

there are two paths or channels which can function simultaneously independent of each other, each connected to a specific handpiece, use of which may be simultaneous or successive within the framework of activity in a single operative field, the two channels can distribute the working fluid and aspirate in pulsed or continuous operation independently of each other, the program sequences producing the appropriate waveforms of the pulsed operation are pre-recorded and specific to a given application. They constitute the optimum for this application, conduit connections and placement are facilitated, sterility is guaranteed at all levels, a special circuit is provided to implement the operational controls of the handpieces based on the pneumatic variation of a fluid, the mechanical means ensure the interruptions of fluid flows under sterile conditions, it is possible to connect the two channels to a single mixed-use handpiece, the apparatus enables periodic firing of short duration, or a single firing of a single pulse, the short duration periodic firing is performed on a tissue made taut by aspiration, incision depth is better controlled, there is improved visibility of the dissection work performed and of the operative field.

BRIEF DESCRIPTION OF THE DRAWINGS

Other characteristics and advantages of the invention will appear in the following description, provided by way of example and accompanied by drawings in which.

DETAILED DESCRIPTION OF THE INVENTION

Figure 1:
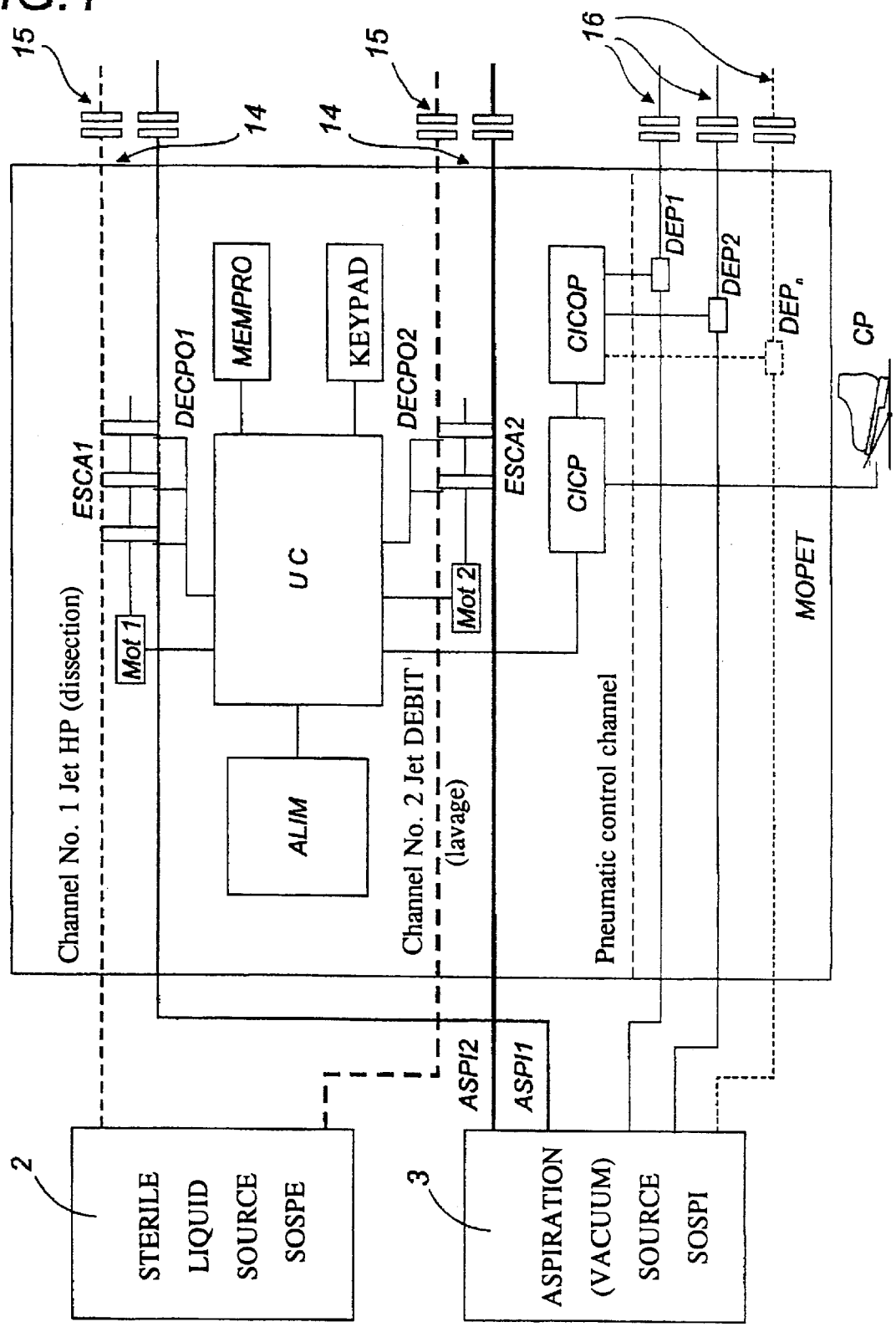
FIG. 1 is a general block diagram of the distribution apparatus according to the invention.
Figure 2:
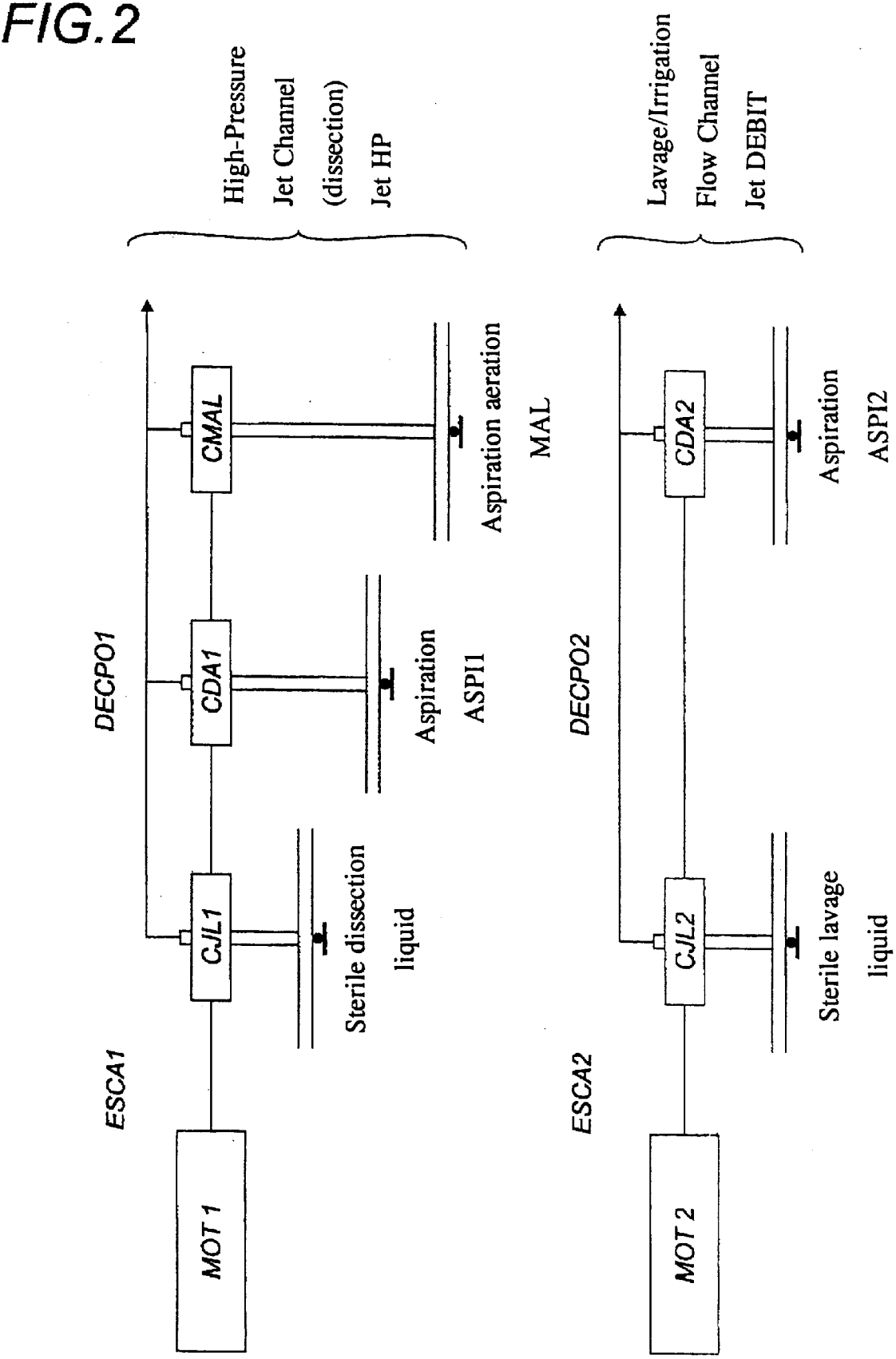
FIG. 2 is a schematic view illustrating the principle of the two basic channels of the apparatus according to the invention.

The distribution and aspiration apparatus according to the invention is made up of at least two basic channels including one for pressurized, in particular high-pressure, sterile liquid, labeled Jet HP, for dissection activities with aspiration, and the other for flowing sterile liquid, labeled Jet DEBIT, for lavage/rinsing or irrigation activities with aspiration. A flow control unit associated with a central unit UC and a memory block MEMPRO control the mode of operation, the regime, and the waveform in each of the channels.

The apparatus according to the invention can be connected to various pressurized liquid sources such as new generation generators and others, but also to a simple elevated reservoir.

Likewise, the apparatus according to the invention can be connected to various aspiration sources, for example, turbine aspirators, vacuum pumps, the vacuum system in the operating theaters, etc.

The liquid used is sterile. It can be, for example, biological serum or a treating solution.

The high working pressure can be, for example, between 10 and 150 bar, or possibly, more specifically, between 100 and 150 bar.

In the drawing, on the one hand, the liquid connections are shown by broken lines, and on the other hand, the aspiration connections are shown by solid lines. The difference in thickness of the lines corresponds to a difference in flow. The thicker the line, the greater the flow of this channel.

As already indicated, the apparatus 1 according to the invention is connected to two sources, one source SOSPE of pressurized sterile liquid 2 and another source SOSPI of depression or aspiration 3. It is depicted in the form of a case 4 containing all the control and management circuits, connections, flow opening/closing control units, as well as a specific module for the pneumatic channels for pneumatic control of the handpieces so equipped, and at least one pedal control.

The case has a front panel 5 grouping certain manual controls 6 and a keypad 7 for communication with the central unit UC. The feeds from the sterile liquid source SOSPE are grouped on one lateral face 8 of the case as a high-pressure input 9 and a flow input 10 as well as the inputs 11 and 12 from the aspiration source into the apparatus. The outputs 14 of the connection lines to the handpieces are grouped on the opposite lateral face 13 of the case as a series of connections such as 15, as well as the connected outputs 16 of the pneumatic control connections with the handpieces so equipped.

For security reasons, the face on which the outputs are grouped, or output face, can be blocked by a door which can be locked and whose panel is used as an interface carrying the output connections of the conduits for connecting the handpieces.

Although the apparatus according to the invention is depicted as a two-channel apparatus, the number of channels of the distribution apparatus according to the invention is limited only by physical and economic considerations.

Figure 3:
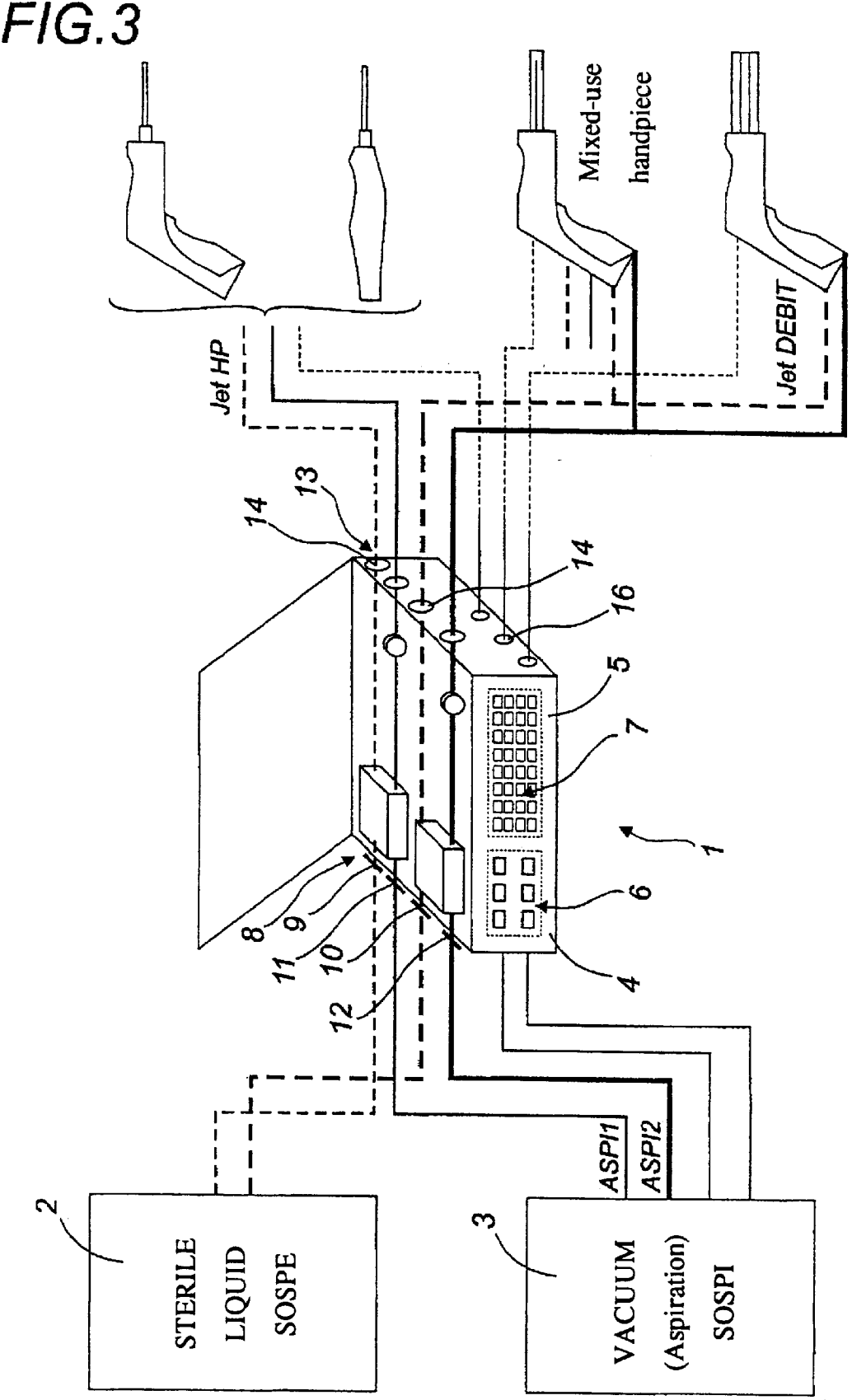
FIG. 3 is a general schematic view depicting the apparatus in a setup for use with the generators and the handpieces.
Figure 4:
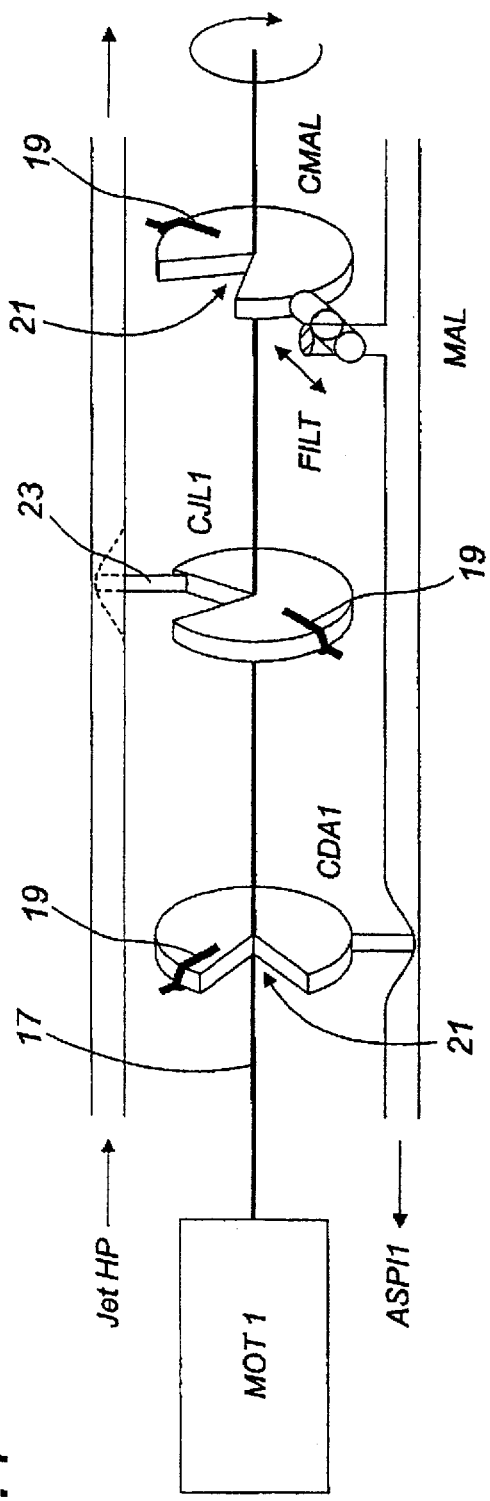
FIGS. 4 and 5 are detailed schematic views of the two basic channels with the corresponding control units.
Figure 5:
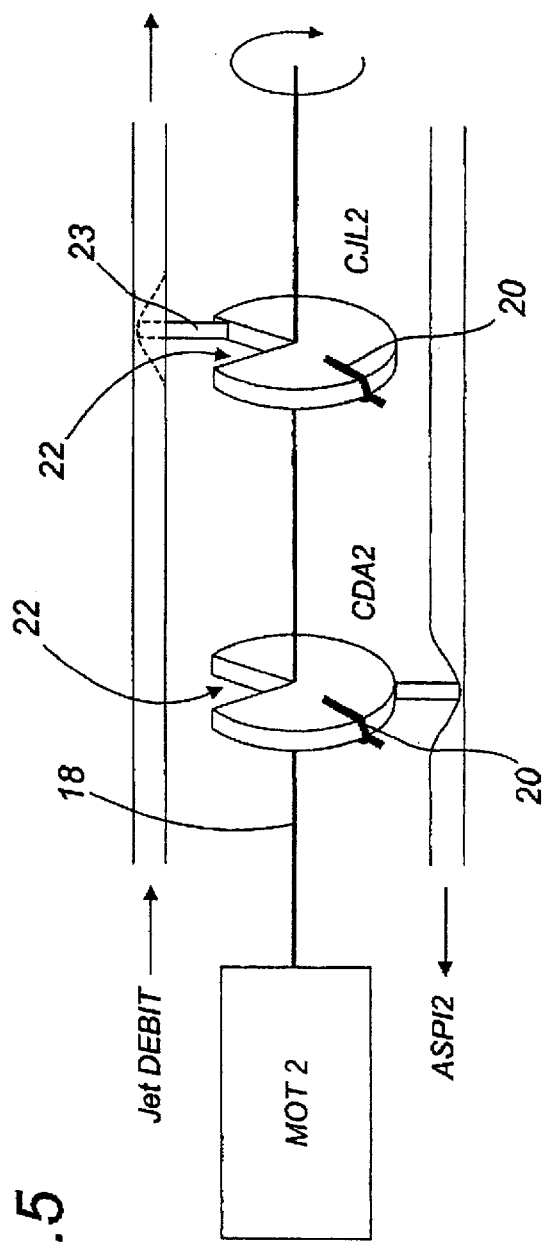

In addition, the two channels of the apparatus can be grouped in the case of a mixed handpiece as shown in FIG. 3, thus offering the functions of dissection in a central block and those of lavage/rinsing or irrigation through a coaxial structure surrounding the central block.

Figure 6:
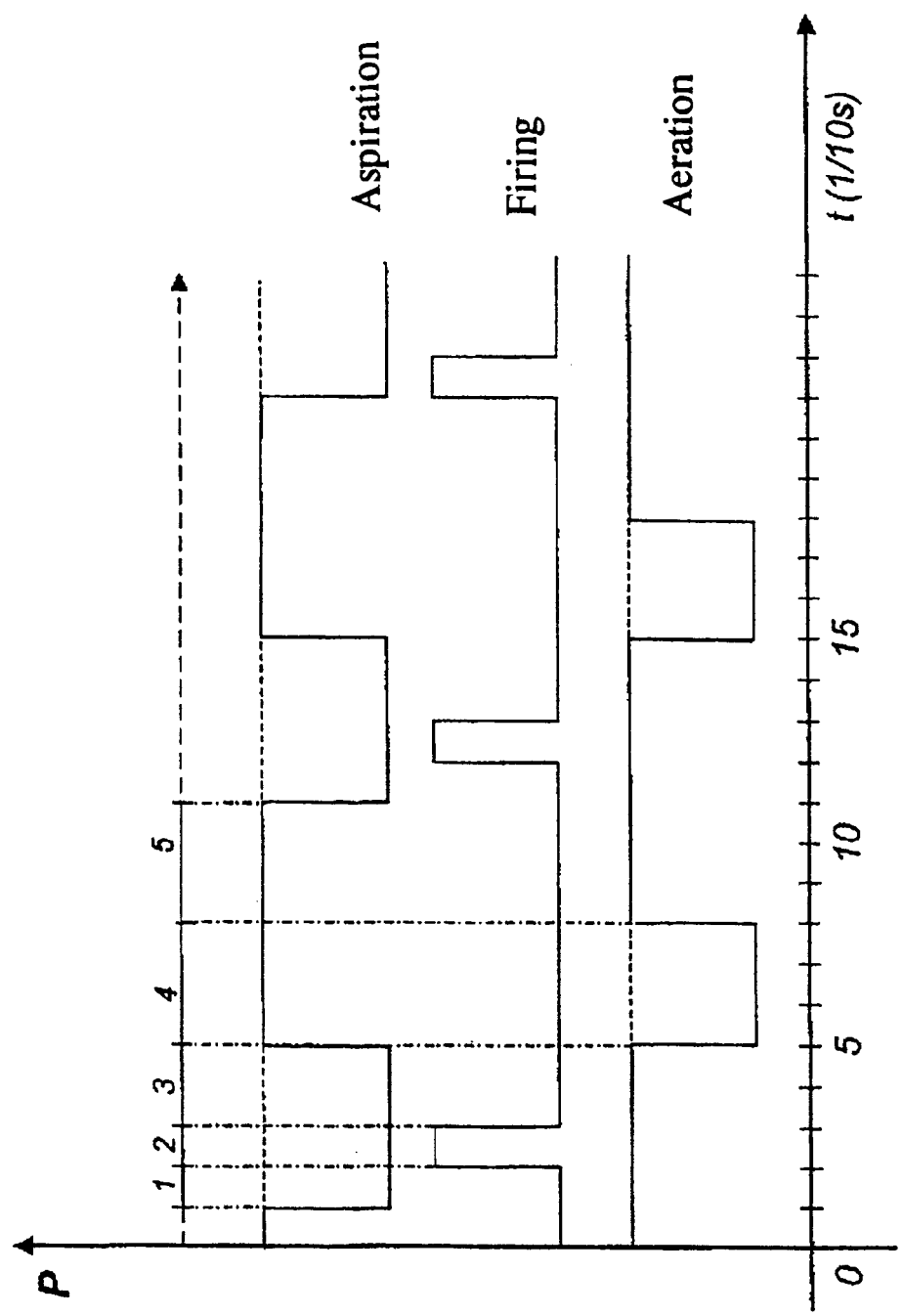
FIG. 6 is a graph showing an example of the development over time of the periodic control actions of the three variables of the dissection channel.

The apparatus according to invention concerns a continuous dissection jet and also a discontinuous jet made up of sets or trains of periodic firing pulses, of which an example of the waveforms developing over time is shown in FIG. 6 and described below, as well as single firing pulse sequences for specific applications.

FIG. 1 shows in a block diagram the makeup of the distribution apparatus according to the invention through its major functions.

A central unit UC controls and manages all the operation of the apparatus. It is connected to the general power supply ALIM and to various peripherals including a keypad KEYPAD, a program memory MEMPRO, a circuit CICOP for exploitation of the pneumatic controls of the handpieces as a function of the program in use, and a circuit CICP for exploitation of a command by one or a plurality of pedals CP.

The central unit UC controls and manages the operation of the control units of each of the two basic channels, channel No. 1 for dissection using a high-pressure jet labeled Jet HP and channel No. 2 for lavage by drainage according to an adjustable flow labeled Jet DEBIT.

These control units are control means for opening/closing the flows in the fluid connections of the apparatus to the handpieces.

The control units, in the example shown, are two electro-mechanical units ESCA1 and ESCA2, for each of the channels No. 1 and No. 2, respectively.

These units are implemented, in the example shown, as cam arrangements mounted for a single group of cams on a single shaft 17 or 18, each driven by an electric motor MOT1 and MOT2, respectively, specific to each channel, each supplied through the central unit UC from the power supply ALIM.

As shall be seen in the following, these motors can be, for example, of the DC type referred to as variable frequency.

Position detectors such as 19 and 20 for each channel are installed in the vicinity of the cams. They inform the central unit UC via lines DECPO1 and DECPO2 concerning the positions of the cams of the two channels No. 1 and No. 2.

The cams have, for example, like those depicted, the form of solid circular disks with an angular recessed sector 21 or 22, with a fixed or adjustable angular opening. The edge of the disk operates by acting on a means of sterile closing/opening of the conduit controlled either directly or through the intermediary of a movable part 23. This movable part 23 may be a lever, a pin, a blade, a rod, or the like activated by an alternating movement between a closing position and a position freeing the conduit. Since these conduits are flexible for the transport of the sterile fluid under sterile conditions or for the aspiration channel, blockage by pinching, collapsing or compressing, or another total restriction by elastic deformation from the outside is used.

Thus, as shown, the cam can directly or indirectly activate a pin or a lever acting to pinch or to collapse or compress the flexible conduit through which the pressurized liquid or the flowing liquid or the gaseous suction fluid of the aspiration channel passes to produce the periodic pulses of the pulsed operation.

The advantage of this type of control is its guaranteed total sterility at the level of the closing/opening switching of the conduits.

To guarantee that the angular shifts between the cams are maintained, the cams on a same channel are mounted on a same shaft provided with longitudinal structures, for example, a fluted shaft.

The free angular section of each cam corresponds to an inactive state of the actuation part on the conduit, i.e., to passage of the fluid. This sector is fixed or adjustable so as to be able to modify the duration of action of the jet. The frequency of repetition of the periodic phenomenon, i.e., the drive pattern, is defined by the central unit UC based on operational programs predefined and recorded in MEMPRO, corresponding to the optimum values derived through representative trials of typical cases of use. Thus, cyclic relationships are defined depending on the medical and surgical specialties and the specific modes of intervention.

These relationships can be modified by changing the angular shift between the cams. To this aim, the cams can be disassembled from the fluted shaft and mounted again with different angular shifts, or the shaft can be provided with smooth intermediary portions on which one or two cams can be freely rotated.

One of the characteristics of the closing/opening control units is to be able to switch into a continuous operation mode, either only for the pressurized liquid jet or for aspiration as well, by means of a limited angular displacement of the common shaft, for example a fluted shaft, on which the cams are mounted with or without a localized shift between them.

Special handpieces with different types of manual controls, in particular pneumatic controls based on pressure or depression discontinuity or discontinuities used as a control signal, may be connected to the apparatus according to invention.

According to these controls, conduits connected to the pressure or depression source are used to initiate a change in pressure or depression by means of a finger action of the user to serve as a control signal.

An annexed module MOPET relates to the channels of the pneumatic controls of the handpieces. A plurality of from 1 to n conduits from the aspiration source SOSPI, designed to be connected as pneumatic control conduits for the handpieces with this type of control, pass through this unit.

Each control conduit line includes a sensor or a detector DEP1, DEP2 . . . DEPn sensitive to a pressure and/or flow variation and connected via the CICOP circuit to the central unit UC.

The pressure discontinuity signals are interpreted by the central unit UC and executed in accordance with the internal program.

As for the sensors or detectors, they may be electrical, magnetic, resistance contacts, or other, detectors and sensors sensitive to pressure, but also flow-sensitive elements. A change in these or the signal that they can emit will be translated into a control pulse.

The number of successive pulses can correspond to a control code or to a progression in the intensity of the value controlled.

Numerous values can thus be controlled relative to the functioning of the handpieces, for example, pressure, flow rate, aspiration, and firing pulse number.

The number of pneumatic control lines is not restricted. It corresponds to the needs of the handpieces, the total number of which determines the capacity of the apparatus according to the invention.

The closing/opening control units ESCA1 and ESCA2 of the conduits of the dissection and lavage channels will now be described in detail with reference to FIGS. 2 to 5 relative to these channels.

Channel No. 1 DISSECTION

The control unit of this channel acts on a high-pressure flexible conduit Jet HP, on a flexible aspiration conduit ASPI1, and on an aeration MAL through a filter FILT providing for the release of the aspiration.

The control unit of this channel consists of a DC motor MOTI referred to as a variable frequency motor driving three cams on the same shaft, for example a fluted shaft, activating devices for closing and freeing a high-pressure liquid conduit Jet HP and aspiration conduit ASPI1.

Each of the cams is specialized. A first high-pressure liquid jet cam CJL1 which controls the high-pressure firing, an aspiration cam CDA1 which controls the aspiration, and an aeration cam CMAL which controls the periodic aeration MAL on the aspiration conduit ASPI1 are distinguished. Each cam has a solid angular sector and a recessed sector. The solid sector controls a conduit-closing device, for example, with a plunger.

The control unit ESCA1 of the dissection channel may include only the two cams CJL1 and CDA1 enabling periodic continuation of the firing without intermediate relaxation of the tissue, i.e., without periodic aeration MAL.

It is also possible to periodically control the relaxation of the tissue by neutralization of the suction from the depression source by means other than periodic aeration of the depression conduit.

The control unit can function in a continuous jet or a pulsed jet mode. In the former case, the cams are set in fixed position in a given configuration. In the second case, the motor MOT1 is operated so as to rotate in a continuous mode at a given constant speed causing a pulsed operation defined by the speed of rotation of the motor, by the respective positions of the angularly shifted cams, and by the angular opening of the recessed sectors of the cams.

Example of the Operation of the Dissection Channel:

Pulsed Operation:

Upon start-up of the apparatus, the cams are in the open position, i.e., their recessed angular sector is facing the conduits; then the motor MOT1 begins to rotate at a low speed and then reaches the speed corresponding to the frequency of the mode of operation selected.

Continuous Operation:

The apparatus permits continuous operation on the dissection channel. It operates in this case on manual control by localized, limited angular displacements of the cams between a position closing and a position opening the corresponding conduit.

Channel No. 2 LAVAGE

This channel is designed for all the applications requiring flow rather than pressure. This means lavage but also rinsing, irrigation of natural cavities of the human body at the time of surgical operations, and all other applications of this type in the areas of surgery and medicine in general.

The control unit of this channel acts on a flexible sterile liquid transport conduit Jet DEBIT under low pressure according to the flow imposed by the handpiece used and on a flexible aspiration conduit ASPI2 connected to the aspiration source.

The control unit consists of a so-called variable frequency DC motor MOT2 activating the common shaft 18, for example, a fluted shaft, bearing two cams CJL2 and CDA2 fixedly attached to this shaft and angularly shifted relative to each other.

The cams are disposed, for example, in phase opposition, i.e., angularly shifted by an angle of 180°. The motor MOT2 is not operated in continuous rotation like the motor MOT1, but rather in limited angular displacement control between a position opening one of the conduits and a correlative lavage position in which the aspiration is closed, followed by aspiration with closing of the lavage jet To accomplish this, the cams are circular and have a solid angular sector followed by a recessed angular sector according to a defined, fixed or adjustable angular opening.

As previously, the cams activate with their edge by pushing a mechanical blocking apparatus, for example, a guided pushing element: a rod, a bar, etc., which comes into collapsing or compressing contact with the flexible conduit it faces for virtually total closing followed by opening at the time of passage of the recessed sector.

In order to properly regulate the flow by means other than the handpiece or the liquid source, it is possible to provide that the edge of the solid sector on the corresponding cam has a progressive curved shape.

Detectors for detecting the cam position or the presence of the solid sector or the recessed sector at a given location are provided in order to inform the central unit concerning the position and the angular distance or excursion to be controlled. These detectors are shown in the figures in the form of stirrups 20 which are fixed relative to the body of each cam.

Example of Operation of the Lavage Channel:

Upon start-up of the apparatus, the two cams are in the position closing the conduits.

An action on the pneumatic control of the handpieces or on the pedal CP causes rotation of the motor MOT2 until complete opening of the aspiration conduit ASPI2 and stopping of the motor when the recessed section of the depression cam CDA2 is located at the level of the control plunger. At the same time, the liquid conduit Jet DEBIT remains closed.

A new control action causes limited rotation of the motor MOT2 until presentation of the recessed sector of the cam CJL2 of the lavage liquid jet at the level of the control plunger, thus again enabling the passage of the sterile lavage/rinsing liquid. At the same time, the depression conduit closes and remains closed.

In order to improve the reliability of the maintenance of the angular shift between the cams, the use of a fluted common shaft, possibly provided with smooth portions to make it possible to modify the angular shift, is preferred. Of course, the cams comprise a central opening which is complementary to enable the cams to be adjusted on the fluting. It is possible to provide a fluted shaft for each group of cams or a single fluted shaft for all the cams.

For purposes of security and ease, a connection interface can be provided on the conduit output face. This interface can be in the form of a pivoting wall or panel (not shown) forming a blocking door carrying the bases of the connection plugs, which are in turn connected to the ends of the flexible conduits of the apparatus on which the cams act.

This panel makes it possible to cut off, when it is closed and locked, any flow in the supply conduits, and therefore, any unintentional liquid output when the handpieces have not yet been plugged in. The door panel condemns the passage of any flow in the conduits of the apparatus at the level of their ends before the connections, for example, by pinching or folding the conduits. This condemnation is maintained until the door is opened.

The apparatus according to the invention is a multi-functional and multi-use apparatus. However, it is intended in particular to implement on its high-pressure channel No. 1 the method for generating a pulsed-aspirated sterile liquid jet which is the object of a parallel application by the applicant filed on Jun. 18, 1999, which is hereby incorporated by reference.

This method described in the parallel application is characterized in that it implements a pressurized liquid channel and a pneumatic aspiration channel and in that the periodic firing of the pressurized jet is controlled during the periodic application of aspiration.

The method is complemented in that a neutralization of the aspiration by air evacuation is performed periodically immediately after closing the aspiration conduit, for example, by aeration of the aspiration conduit, and for higher-frequency modes of operation, a periodic discharge of the residual pressure on the pressure channel is also preferred.

The major phases characteristic of each period of the pulse set or train according to this method are the following, as identified by reference numerals 1 through 5 in FIG. 6.

phase 1: start of aspiration,
phase 2: firing of the jet under pressure for a short period within the aspiration pulse,
phase 3: continuation of aspiration after firing,
phase 4: aeration during the break in aspiration,
phase 5: continuation of the break in aspiration until the following period.

The following general characteristics are noted by observation of the figures. Firing takes place with a certain delay relative to the beginning of aspiration. Firing takes place preferably within the first half of the width of the aspiration pulse and stops preferably before the beginning of the second half. The aeration occurs after the break in aspiration and preferably but not necessarily immediately after this break.

By way of nonrestrictive example, major characteristic values of the parameters of pulse set of the pressurized pulsed-aerated liquid jet corresponding to that shown in FIG. 6 are indicated below.

repetition rate: 1 Hz
firing pulse width: 100 ms
aspiration pulse width: 400 ms
aspiration pause: 600 ms
aeration pulse width: 300 ms
break between the end of the aspiration pulse and aeration: very slight.

Aeration is short and immediately follows the end of aspiration.

The rising flanks of the pulses have been depicted vertically, which is relatively true here in the case of control by cam and collapsing or compression of a flexible conduit by means of a rod.

Different waveforms are possible.

Thus, the repetition rate of pulsed operation and the pulse width may vary. These variations depend on the surgical application, i.e., the types of intervention, organ or tissue in question, as well as the depth of intervention in the human body.

The controls corresponding to other waveforms are prerecorded in the module MEMPRO. These are waveforms characteristic of a specific surgical application with regard to both the organ in question and the surgical technique.

It should be noted that the more the firing pulse width increases, the more that of the aspiration must increase to be able to completely evacuate the liquid and the residue or residues before the next firing.

What is claimed is:

1. Apparatus for distributing sterile operating liquid with aspiration to at least one handpiece used by an operator in a surgical or medical operation, said apparatus being connected to a pressurized sterile liquid source and to a depression source, said apparatus comprising at least a pressure channel for distributing pressurized sterile liquid with aspiration for dissection activities and a flow channel for distributing flowing sterile liquid with aspiration for lavage/rinsing or irrigation activities, each of said pressure channel and said flow channel comprising a liquid conduit and a depression conduit, each of said pressure channel and said flow channel being connected to one of said at least one handpiece and controlled for opening/closing of each of the liquid conduit and the depression conduit by means of a periodic or continuous flow control unit associated with a memory block, in which predefined modes of operation are recorded, linked with a central unit for generating pulsed or continuous jets in association with manual controls initiated by the operator and originating in said at least one handpiece or other control elements.

2. Apparatus according to claim 1, which comprises means for generating pulsed-aspirated jets.

3. Apparatus according to claim 2, wherein the means for generating pulsed-aspirated jets performs periodic aeration of the aspiration after breaking of this aspiration.

4. Apparatus according to claim 1, wherein the flow control units are electro-mechanical.

5. Apparatus according to claim 4, wherein each of the flow control units comprises two distinct units, each comprising a group of cams comprising at least two cams mounted angularly shifted relative to each other on a common shaft and actuated by a first electric motor for the pressure channel and by a second electric motor for the flow channel.

6. Apparatus according to claim 5, wherein the cams are circular with a solid angular sector and a recessed angular sector.

7. Apparatus according to the claim 6, wherein the recessed sector has an adjustable opening angle.

8. Apparatus according to claim 5, wherein the cams actuate, by the passage between the recessed sector and the solid sector and vice versa, a movable element which, by its displacement, provides for the closing and then the opening of the corresponding liquid or depression conduit.

9. Apparatus according to claim 8, which comprises means for compressing the corresponding liquid or depression conduit which is flexible, so as to close this conduit.

10. Apparatus according to claim 8, which comprises means for pinching the corresponding liquid or depression conduit which is flexible, so as to close this conduit.

11. Apparatus according to claim 5, wherein the pressure channel comprises a liquid conduit cam for opening and closing the liquid conduit, a depression conduit cam for opening and closing the depression conduit, and an aeration cam for periodic aeration of the depression conduit in a rhythm corresponding to pulsed jets, said cams being angularly shifted relative to each other, so as to obtain a pulsed-aspirated jet followed by a release, resulting in relaxation of a tissue in an area where the pulsed-aspirated jet is used.

12. Apparatus according to claim 11, wherein aeration takes place through a filter.

13. Apparatus according to claim 11, wherein the pressure channel includes no aeration.

14. Apparatus according to claim 5, wherein the flow channel comprises a liquid conduit cam for opening and closing the liquid conduit and a depression conduit cam for opening and closing the depression conduit, said cams being angularly shifted relative to each other.

15. Apparatus according to claim 14, wherein the cams are mounted on a same shaft and are angularly shifted relative to each other at an angle of 180°.

16. Apparatus according to claim 5, wherein the cams are equipped with a position detector or sensor or detectors or sensors.

17. Apparatus according to claim 5, wherein the pressure channel comprises means for generating a continuous jet or a periodic pulsed-aspirated jet having adjustable characteristics and means for providing periodic aeration in a rhythm corresponding to the pulsed-aspirated jet.

18. Apparatus according to claim 5, wherein the flow channel operates continuously with simultaneous or successive aspiration and has limited angular cam displacement control.

19. Apparatus according to claim 5, wherein each group of cams is mounted on a fluted common shaft, or all cams are mounted on a single fluted common shaft.

20. Apparatus according to claim 1, wherein the manual controls initiated by the operator and originating in said at least one handpiece are pressure or depression discontinuity controls.

21. Apparatus according to claim 20, wherein the manual controls are depression conduits connecting the depression source to said at least one handpiece and passing through or next to a sensor or detector sensitive to pressure or to flow.

22. Apparatus according to caim 1, wherein at least one of the manual controls is a pedal.

23. Apparatus according to claim 1, wherein said at least one handpiece is a mixed-use handpiece combining primary functions of dissection and of lavage/rinsing or irrigation.

24. Apparatus according to claim 1, wherein an output face for output of the conduits connected to said at least one handpiece comprises a blocking pivoting panel carrying at least one connection part for the conduits connecting to said at least one handpiece, and the blocking pivoting panel blocks the passage of any flow in the conduits connecting to said at least one handpiece in the area inside the apparatus before said at least one connection part.

* * * * *